(12) United States Patent
Rho et al.

(10) Patent No.: US 10,208,009 B2
(45) Date of Patent: Feb. 19, 2019

(54) HYDROXYL PYRANONE COMPOUND, METHOD FOR PRODUCING SAME, AND COSMETICS COMPOSITION COMPRISING COMPOUND

(71) Applicant: AMOREPACIFIC CORPORATION, Seoul (KR)

(72) Inventors: Ho Sik Rho, Yongin-si (KR); Jae Won Yoo, Yongin-si (KR); Yong Jin Kim, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 15/780,421

(22) PCT Filed: Nov. 30, 2016

(86) PCT No.: PCT/KR2016/013927
§ 371 (c)(1),
(2) Date: May 31, 2018

(87) PCT Pub. No.: WO2017/095121
PCT Pub. Date: Jun. 8, 2017

(65) Prior Publication Data
US 2018/0354925 A1    Dec. 13, 2018

(30) Foreign Application Priority Data

Dec. 1, 2015   (KR) .................. 10-2015-0169644
Nov. 28, 2016  (KR) .................. 10-2016-0159460

(51) Int. Cl.
*C07D 309/40*   (2006.01)
*A61Q 19/08*    (2006.01)
*A61K 8/49*     (2006.01)
*C07D 309/34*   (2006.01)

(52) U.S. Cl.
CPC ............ *C07D 309/40* (2013.01); *A61K 8/498* (2013.01); *A61Q 19/08* (2013.01); *C07D 309/34* (2013.01)

(58) Field of Classification Search
CPC ....... C07D 309/40; A61K 8/498; A61Q 19/08
See application file for complete search history.

(56) References Cited

U.S. PATENT DOCUMENTS

| | | |
|---|---|---|
| 4,990,330 A | 2/1991 | Oyama |
| 6,916,844 B2 | 7/2005 | Roh et al. |
| 2016/0324824 A1 | 11/2016 | Rho et al. |

FOREIGN PATENT DOCUMENTS

| | | |
|---|---|---|
| EP | 0419901 A1 | 4/1991 |
| JP | 59-033207 A | 2/1984 |
| JP | H07118134 A | 5/1995 |
| JP | H07242527 A | 9/1995 |
| JP | 2003155283 A | 5/2003 |
| KR | 10-048668 B1 | 4/2005 |
| KR | 10-0494535 B1 | 6/2005 |
| KR | 10-2013-0107865 A | 10/2013 |
| KR | 20150062443 A | 6/2015 |
| KR | 10-2015-0086681 A | 7/2015 |

OTHER PUBLICATIONS

Xu et al., "The use of small interfering RNAs to inhibit adipocyte differentiation in human preadipocytes and fetal-femur-derived mesenchymal cells", Experimental Cell Research, 2006, vol. 312, pp. 1856-1864.
Pittenger et al., "Multilineage Potential of Adult Human Mesenchymal Stem Cells", Science, 1999, vol. 284, pp. 143-146.
Da Silva Meirelles e al., "Mesenchymal stem cells reside in virtually all post-natal organs and tissues", Journal of Cell Science, 2006, vol. 119, No. 2204-2213.
Rho et al., "Kojyl cinnamate ester derivatives promote adiponectin production during adipogenesis in human adipose tissue-derived mesenchymal stem cells", Bioorganic & Medicinal Chemistry Letters, 2014, vol. 24, pp. 2141-2145.
International Search Report for International Application No. PCT/KR2016/013927 (2 Pages) (dated Mar. 6, 2017).
The extended European search report, Application No. 16871017.6, dated Sep. 26, 2018.

*Primary Examiner* — Timothy R Rozof
(74) *Attorney, Agent, or Firm* — Lucas & Mercanti, LLP

(57) ABSTRACT

The present invention relates to a novel hydroxyl pyranone compound, a method for producing same, and a cosmetic composition having the compound. The hydroxyl pyranone compound according to the present invention exhibits markedly improved effectiveness compared to the conventional adipocyte differentiation-promoting material, and thus is preferably included as an active ingredient in a cosmetic composition for increasing skin volume or elasticity.

4 Claims, No Drawings

HYDROXYL PYRANONE COMPOUND, METHOD FOR PRODUCING SAME, AND COSMETICS COMPOSITION COMPRISING COMPOUND

CROSS-REFERENCE TO RELATED APPLICATIONS

This application is a 371 of PCT/KR2016/013927, filed Nov. 30, 2016 which claims the benefit of Korean Patent Application No. 10-2015-0169644 filed Dec. 1, 2015 and Korean Patent Application No. 10-2016-0159460 filed Nov. 28, 2016, the contents of each of which are incorporated herein by reference.

TECHNICAL FIELD

The present invention relates to a novel hydroxyl pyranone compound having adipocyte differentiation promoting ability, a method for preparing the same, and a cosmetic composition containing the same as an active ingredient.

BACKGROUND ART

The basic structure of the skin is maintained by subcutaneous adipose tissue. The subcutaneous adipose tissue plays a critical role in maintaining the volume and strength of the skin. Accordingly, in order to maintain and improve the volume and elasticity of the skin, increasing the volume of the adipose tissue rather than imparting the elasticity to the dermis or epidermis in the outer layer of the skin can be a fundamental solution.

Specifically, as the aging of the human body progresses, wrinkles are generated on the skin, and at the same time, the elasticity of the skin is also reduced. The aging of the skin, such as wrinkle formation and decreased elasticity, is a complex phenomenon caused by the decrease in the activity of adipocytes or hence the decrease in lipid droplets along with the degradation and reduction of skin fibers such as collagen and elastin, which are skin components. Therefore, if the lipid droplets can be produced and accumulated by promoting adipocyte differentiation in humans, the wrinkles and elasticity of the skin can be improved.

Recently, upon reviewing various research trends using adipocytes, currently, studies using adipocytes have been actively conducted in a variety of fields including studies for increasing the volume feel and elasticity of the skin. Among them, preadipocytes are widely used because they have the property of differentiating into adipocytes by differentiation inducers such as insulin.

Particularly, among these preadipocytes, mesenchymal stem cells for adipocytes have recently received attention. Since adipose-derived mesenchymal stem cells can be differentiated using methods similar to those used to differentiate preadipocytes into adipocytes (*Exp. Cell Res.* 2006, 312, 1856-1864), they are widely used in the study of adipocyte differentiation (*Science* 1999, 284, 143-146). In addition, such adipose-derived mesenchymal stem cells are known to be able to differentiate not only into adipocytes but also into other types of cells such as chondrocytes and bone cells (*J. Cell Sci.* 2006, 119, 2204-2213), and are distributed in most tissues of the body, and thus are thought to be infinitely useful.

In the meantime, various attempts have been made to promote the differentiation of adipocytes in order to improve the volume and elasticity of the skin. According to the results of such previous studies, it has been reported that cinnamic acid compounds show adipocyte differentiation promoting effect. In addition, there has been a report that hydroxyl pyranone derivatives including cinnamic acid mother nucleus significantly increase adipocyte differentiation promoting effect compared to cinnamic acid. In this regard, it was confirmed that as a result of analyzing the structural active correlations of various derivatives, the double bond of cinnamic acid plays an important role.

However, since the effect of increasing the volume and elasticity of the skin in the human body, when incorporating these materials for promoting adipocyte differentiation into actual cosmetic compositions, etc. was still insufficient, it has been difficult for consumers to obtain maximum satisfaction related to the use of cosmetic composition.

Accordingly, it was necessary to develop a material for promoting adipocyte differentiation with improved efficacy.

PRIOR ART

Hydroxy pyranone derivative and preparation method thereof (Korea Patent No. 10-0482668)

DISCLOSURE

Technical Problem

In order to solve the above-described problems, the inventors of the present invention have conducted various studies on the compounds capable of improving the adipocyte differentiation promoting effect over the existing compounds based on the above-mentioned previous research results. As a result, the inventors have completed the present invention by preparing a novel compound comprising a mother nucleus of 3-(2,6,6-timethyl-cyclohex-2-enyl)-propenoic acid among the hydroxyl pyranone compounds, and then confirming that the novel compound improves the differentiation promoting effect of adipocytes.

Therefore, it is an object of the present invention to provide a novel hydroxyl pyranone compound which improves the differentiation promoting effect of adipocytes.

In addition, it is another object of the present invention to provide a method for preparing the novel hydroxyl pyranone compound.

In addition, it is still another object of the present invention to provide a cosmetic composition comprising the novel hydroxyl pyranone compound as an active ingredient.

Technical Solution

According to an object of the present invention, the present invention provides a hydroxyl pyranone compound represented by the following Formula 1:

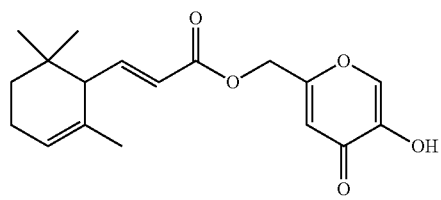

[Formula 1]

According to another object of the present invention, the present invention provides a method for preparing a hydroxyl pyranone compound of Formula 1 by reacting a compound of the following Formula 2 and a compound of the following Formula 3, which is represented by the following Reaction Scheme 1:

[Reaction Scheme 1]

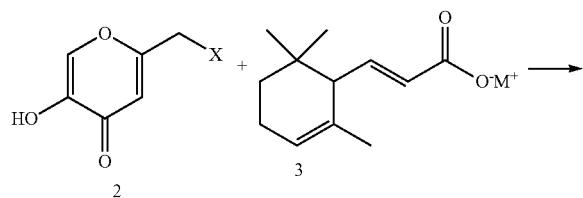

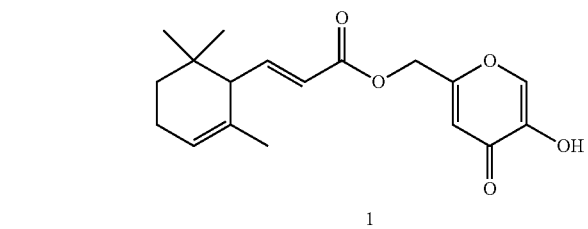

wherein X and M are as described in the specification.

According to still another object of the present invention, the present invention provides a cosmetic composition comprising a hydroxyl pyranone compound represented by Formula 1 as an active ingredient.

Advantageous Effects

The hydroxyl pyranone compound according to the present invention has an enhanced adipocyte differentiation promoting effect compared to the conventional seletinoid G or other adipocyte differentiation promoting compounds.

Specifically, since the compounds of the present invention can promote the phenomenon of differentiation of human mesenchymal stem cells into adipocytes and thus induce lipid droplets, thereby enhancing the volume and elasticity of the skin, it can be formulated into various cosmetic products to improve the satisfaction of consumers.

BEST MODE

Hereinafter, the present invention will be described in detail.

The present invention provides a novel hydroxyl pyranone compound represented by the following Formula 1:

[Formula 1]

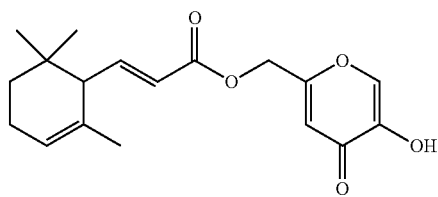

The IUPAC name of the hydroxyl pyranone compound of Formula 1 is 3-(2,6,6-trimethyl-cyclohex-2-enyl)-propenoic acid 5-hydroxy-4-oxo-4H-pyran-2-ylmethyl ester.

The compound of Formula 1 is an off-white solid compound at room temperature.

The hydroxyl pyranone compounds according to the present invention may include isomers. At this time, the "isomers" particularly may include optical isomers (e.g., essentially pure enantiomers, essentially pure diastereomers, or mixtures thereof), as well as conformation isomers (i.e., isomers differing only in the angle of one or more chemical bonds), position isomers (particularly tautomers) or geometric isomers (e.g., cis-trans isomers).

The compound represented by Formula 1 is prepared by reacting a pyranone compound of Formula 2 and a cyclohexenyl ester compound of Formula 3 as shown in the following Reaction Scheme 1:

[Reaction Scheme 1]

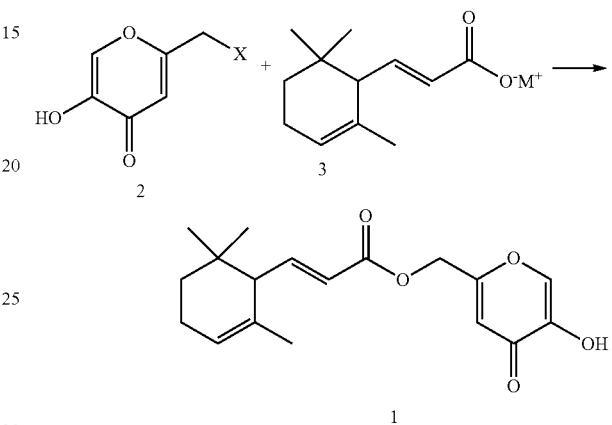

wherein X is a halogen element and M is Li, Na or K.

Referring to Reaction Scheme 1, the compound of Formula 1 is prepared by a coupling reaction between a halogen element in the pyranone compound and a metal in the cyclohexenyl ester compound.

Herein, X in the pyranone compound of Formula 2 is a halogen element. At this time, the halogen element may be F, Cl, Br, or I, preferably Cl. The compound of Formula 2 is commercially available or can be prepared directly.

In the Example of the present invention, 5-hydroxy-2-(chloromethyl)-4H-pyran-4-one in which X is Cl was used, which was prepared directly by reacting 5-hydroxy-2-(hydroxymethyl)-4H-pyran-4-one with thionyl chloride ($SOCl_2$).

In addition, the cyclohexenyl ester compound of Formula 3 is present in a form in which a cation ($M^+$) is bonded to the carboxyl group of 3-(2,6,6-timethyl-cyclohex-2-enyl)-propenoic acid, which is an ionized salt form of 3-(2,6,6-timethyl-cyclohex-2-enyl)-propenoic acid.

The cation ($M^+$) may be any one selected from the group consisting of $Li^+$, $Na^+$, and $K^+$ Preferably, the compound may be an ion-binding compound of 3-(2,6,6-timethyl-cyclohex-2-enyl)-propenoic acid and $Na^+$, and it may be prepared by dissolving 3-(2,6,6-timethyl-cyclohex-2-enyl)-propenoic acid and sodium hydroxide in methanol and ionizing them and then distilling methanol.

In a preferred embodiment of the present invention, the hydroxyl pyranone compound of Formula 1 was prepared through an ester linkage of 5-hydroxy-2-(chloromethyl)-4H-pyran-4-one as the compound of Formula 2 and sodium 3-(2,6,6-timethyl-cyclohex-2-enyl)-propenoate as the compound of Formula 3.

At this time, the reaction is not particularly limited in the present invention and may be carried out under conditions in which the halogen-metal bond reaction can be made sufficiently.

The reaction may be carried out at the reflux temperature of the solvent, for example, at 50 to 250° C. for 0.5 to 5 hours, preferably for 1 to 3 hours.

At this time, the solvent may be any solvent capable of sufficiently dissolving the compounds of Formulas 2 and 3, and for example, may be any one selected from the group consisting of N,N-dimethylformamide (DMF), tetrahydrofuran (THF), dimethyl sulfoxide (DMSO), acetonitrile, dioxane, benzene, toluene, ether, methanol, hexane, cyclohexane, pyridine, N-methyl pyrrolidone, and combinations thereof, and may preferably be DMF.

After the reaction, a high-purity compound may be obtained through a post-treatment such as ordinary washing, drying, purifying and the like after the solvent is distilled.

The hydroxyl pyranone compound of Formula 1 according to the present invention can be applied to various fields and may preferably be used in cosmetic compositions as an active ingredient. At this time, the compound of Formula 1 promotes adipocyte differentiation, and thus lipid droplets can be generated and accumulated, thereby improving wrinkles and elasticity of the skin When the hydroxyl pyranone compound is used in a cosmetic composition as an active ingredient, the content thereof varies depending on the formulation and may be used in an amount of from 0.001 to 99% by weight. When the active ingredient is contained in the above range, it is not only suitable for exhibiting the intended effect of the present invention but also can satisfy both the stability and solubility of the composition, and it can be most efficient in terms of cost-effectiveness.

The cosmetic composition may be prepared in any of the formulations conventionally manufactured in the prior art and may be formulated as, for example, but not limited to, solution, suspension, emulsion, paste, gel, cream, lotion, powder, oil, powder foundation, emulsion foundation, wax foundation and spray. More specifically, the cosmetic composition may be prepared as a formulation of sun cream, softening lotion, astringent lotion, nutrient lotion, nutrient cream, massage cream, essence, eye cream, pack, spray or powder.

In addition, the cosmetic composition according to the present invention may include fats, organic solvents, solubilizer, thickeners, gelling agents, softeners, antioxidants, suspending agents, stabilizers, foaming agents, perfumes, surfactants, water, ionic or non-ionic emulsifiers, fillers, metal ion sequestrants and chelators, preservatives, vitamins, screening agents, humectants, essential oils, dyes, pigments, hydrophilic or lipophilic activating agents and lipid vesicles or additives commonly used in the field of cosmetics or dermatology, such as any other component commonly used in cosmetics. The additives may be introduced in amounts commonly used in the field of cosmetics or dermatology.

When the formulation is a paste, a cream or a gel, animal oils, vegetable oils, wax, paraffin, starch, tragacanth, cellulose derivative, polyethylene glycol, silicone, bentonite, silica, talc or zinc oxide, etc. may be used as a carrier component.

When the formulation is a powder or a spray, lactose, talc, silica, aluminum hydroxide, calcium silicate or polyamide powder may be used as a carrier component. In particular, the spray may additionally comprise propellants such as chlorofluorohydrocarbon, propane/butane or dimethyl ether.

When the formulation is a solution or an emulsion, solvent, solubilizing agents or emulsifying agents may be used as a carrier component. For example, water, ethanol, isopropanol, ethyl carbonate, ethyl acetate, benzyl alcohol, benzyl benzoate, propylene glycol, 1,3-butyl glycol oil, glycerol aliphatic ester, polyethylene glycol or a fatty acid ester of sorbitan may be used.

When the formulation is a suspension, liquid diluents such as water, ethanol or propylene glycol, suspending agents such as ethoxylated isostearyl alcohol, polyoxyethylene sorbitol ester and polyoxyethylene sorbitan ester, or microcrystalline cellulose, aluminum metahydroxide, bentonite, agar, tragacanth, etc. may be used as a carrier component.

Hereinafter, examples and test examples are provided for further explanation of the contents and effects of the present invention. However, the following contents are only examples of the present invention, and the scope and effect of the present invention are not limited thereto.

Example: Preparation of 3-(2,6,6-trimethyl-cyclohex-2-enyl)-propenoic acid 5-hydroxy-4-oxo-4H-pyran-2-ylmethyl ester 3-(2,6,6-trimethyl-cyclohex-2-enyl)-propenoic acid 5-hydroxy-4-oxo-4H-pyran-2-ylmethyl ester which is the hydroxyl pyranone compound of Formula 1 of the present invention was prepared according to the following Reaction Scheme 2.

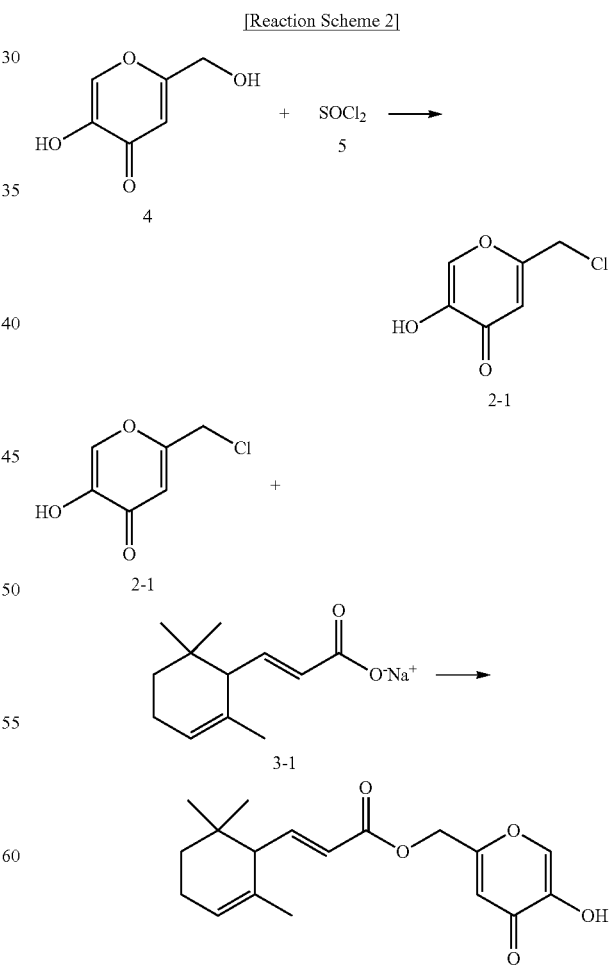

The detailed procedure for carrying out the Reaction Scheme 2 was as follows.

50 g of 5-hydroxy-2-(hydroxymethyl)-4H-pyran-4-one (0.35 mmol) was dissolved in 250 ml of N,N-dimethylformamide and cooled in an iced water bath at 10° C. and then 50 g (0.42 mol) of thionyl chloride was added dropwise over 30 minutes. After stirring at room temperature for 2 hours, the reaction solution was added to 2000 ml of an iced water. The resulting solid was filtered, and the solid (filtered material) was dissolved in 1000 ml of ethyl acetate. Magnesium sulfate and activated charcoal were added thereto for drying and decolorization and were filtered, and then the filtrate was concentrated and nucleic acid was added to obtain crystals. The resulting crystals were dried under vacuum to obtain 39.5 g (70%) of the reaction product, 5-hydroxy-2-(chloromethyl)-4H-pyran-4-one of the Formula 2-1 as a yellow solid.

Subsequently, 5 g (0.026 mol) of 3-(2,6,6-timethyl-cyclohex-2-enyl)-propenoic acid and 1.3 g (0.031 mol) of sodium hydroxide were dissolved in 40 ml of methanol. After the methanol was distilled off, the remaining residue was dissolved in 70 ml of N,N-dimethylformamide to prepare a compound of Formula 3-1.

To the compound of Formula 3-1, 4.2 g (0.026 mol) of 5-hydroxy-2-(chloromethyl)-4H-pyran-4-one of the prepared Formula 2-1 was added and then heated and stirred in an oil bath at 110° C. for 2 hours. The solvent was distilled off and the residue was dissolved in 300 ml of ethyl acetate, and then the ethyl acetate solution was washed with 5% hydrochloric acid and distilled water, and magnesium sulfate and activated carbon were added to dry and discolor the solution. Subsequently, the insoluble matters were filtered off and the filtrate was evaporated under reduced pressure to give 5.9 g (69% yield) of the reaction product as an off-white solid.

TLC (ethyl acetate:hexane=1:1) Rf=0.43

$^1$H NMR (DMSO-$d_6$, δ): 9.22 (s, 1H), 8.09 (s, 1H), 6.75 (m, 1H), 6.46 (s, 1H), 5.95 (d, 1H, J=16.2 Hz), 5.50 (s, 1H), 5.02 (s, 2H), 2.45 (m, 2H), 2.00 (m, 2H), 1.42 (m, 1H), 1.20 (m, 2H), 0.88 (s, 3H), 0.80 (s, 3H)

Test Example: Confirmation of Adipocyte Differentiation Promoting Effect

In order to examine the adipocyte differentiation promoting effect of the compounds prepared in the Example, the following test was carried out.

Adiponectin is a typical protein hormone secreted from adipocytes. It has been reported that as adipocytes are differentiated, the expression of adiponectin is increased. Therefore, the adipocyte differentiation promoting effect was confirmed by measuring the amount of adiponectin expressed in the cell culture medium when treated with the novel compound of the present invention, which is an indicator of adipocyte differentiation promoting.

The adipocyte differentiation was performed by culturing human adipose tissue derived mesenchymal stem cells (hAT-MSCs) from Lonza Inc. (Walkersville, Md., USA) according to Lonza's guidelines. The adipocyte differentiation was carried out using the method recommended by Lonza Inc., except that the adipocyte differentiation of adipose-derived mesenchymal stem cells is induced by using troglitazone (TRO) instead of indomethacin. Specifically, the mesenchymal stem cells were differentiated into adipocytes by adding the medium for adipocyte differentiation (hereinafter referred to as IDX), which was prepared by mixing 1 g/ml of insulin, 1 M of Dexamethasone (DEXA), 0.5 mM of isobutylmethylxanthine (IBMX) and 2 M of TRO, to the culture medium of mesenchymal stem cells, and then culturing it.

In order to determine the expression level of adiponectin, after the medium for adipocyte differentiation was collected on the 14th day of differentiation, the amount of adiponectin was quantified using the Adiponectin ELISA Kit (R & D systems, Cat. No. DY1065) (each data value was corrected by the control group). The specific measurement method using Adiponectin ELISA Kit was as follows.

First, the capture antibody was reacted in a 96-well plate, washed with washing buffer solution, and then the material shown in Table 1 below was added and reacted at room temperature for 2 hours. Thereafter, while washing three times every time when going through each step, the detection antibody, the HRP enzyme, the substrate solution, and the stop solution were added in order and reacted for the time indicated in the protocol. After the final reaction, the absorbance was measured at a wavelength of 450 nm using a spectrophotometer.

The results obtained through the above process are shown in Table 1.

TABLE 1

| Treating material | Adiponectin (pg/ml, Avg ± S.D.) |
|---|---|
| Untreated group | 31 ± 10 |
| IDX treated group | 303 ± 40 |
| IDX + Glibenclamide | 1920 ± 100 |
| IDX + Kojic acid (400M) | 303 ± 98 |
| IDX + Seletinoid G (60M) | 1505 ± 109 |
| IDX + compound of example (Formula 1) (60M) | 1730 ± 120 |

Referring to Table 1, when treated with kojic acid in the experiment for confirming the expression level of adiponectin, the expression level of adiponectin was not increased. On the other hand, when treated with the hydroxy pyranone derivative of the compound of Formula 1 of Example according to the present invention, it was confirmed that the expression level increases almost similarly to that with Glibenclamide, which is a positive control group. This corresponds to a significantly increased expression level even in comparison with the case of treatment with a conventional adipocyte differentiation promoting compound.

Therefore, it was confirmed that the hydroxyl pyranone compound of Formula 1 according to the present invention has excellent adipocyte differentiation promoting ability, and the cosmetic composition containing it as an effective component can increase the volume and elasticity of the skin.

Hereinafter, formulation examples of cosmetic compositions according to still another aspect of the present disclosure are provided. However, the cosmetic formulations comprising the hydroxyl pyranone compound according to the present invention are not limited only to the following examples.

Formulation Example 1 (Lotion)

A lotion was prepared using the compositions shown in Table 2 below according to a conventional method.

TABLE 2

| Component | Content (wt. %) |
|---|---|
| Compound of Formula 1 (Example) | 0.1 |
| Glycerine | 3.0 |
| Buthylene glycol | 2.0 |
| Propylene glycol | 2.0 |
| Carboxyvinyl polymer | 0.1 |
| PEG 12 nonylphenyl ether | 0.2 |
| Polysorbate 80 | 0.4 |
| Ethanol | 10.0 |
| Triethanolamine | 0.1 |
| Preservative, Pigment, Perfume | q.s. |
| Purified water | remainder |

Formulation Example 2 (Milk Lotion)

A milk lotion was prepared using the compositions shown in Table 3 below according to a conventional method.

TABLE 3

| Combined component | Content (wt. %) |
|---|---|
| Compound of Formula 1 (Example) | 1.0 |
| Glycerine | 3.0 |
| Buthylene glycol | 3.0 |
| Propylene glycol | 3.0 |
| Carboxyvinyl polymer | 0.1 |
| Bee wax | 4.0 |
| Polysorbate 60 | 1.5 |
| Caprlic/capric triglyceride | 5.0 |
| Squalane | 5.0 |
| Sorbitansesquiolate | 1.5 |
| Liquid paraffin | 0.5 |
| Cetearyl alcohol | 1.0 |
| Triethanolamine | 0.2 |
| Preservative, Pigment, Perfume | q.s. |
| Purified water | remainder |

Formulation Example 3 (Nutrient Cream)

A nutrient cream was prepared using the compositions shown in Table 4 below according to a conventional method.

TABLE 4

| Component | Content (wt. %) |
|---|---|
| Compound of Formula 1 (Example) | 2.0 |
| Polysorbate 60 | 1.5 |
| Sorbitansesquiolate | 0.5 |
| PEG 60 hydrogenated castor oil | 2.0 |
| Liquid paraffin | 10. |
| Squalane | 5.0 |
| Caprlic/capric triglyceride | 5.0 |
| Glycerine | 5.0 |
| Buthylene glycol | 3.0 |
| Propylene glycol | 3.0 |
| Triethanolamine | 0.2 |
| Preservative, Pigment, Perfume | q.s. |
| Purified water | remainder |

Formulation Example 4 (Massage Cream)

A massage cream was prepared using the compositions shown in Table 5 below according to a conventional method.

TABLE 5

| Component | Content (wt. %) |
|---|---|
| Compound of Formula 1 (Example) | 1.0 |
| Bee wax | 10.0 |
| Polysorbate 60 | 1.5 |
| PEG 60 hydrogenated castor oil | 2.0 |
| Sorbitansesquiolate | 0.8 |
| Liquid paraffin | 40.0 |
| Squalane | 5.0 |
| Caprlic/capric triglyceride | 4.0 |
| Glycerine | 5.0 |
| Buthylene glycol | 3.0 |
| Propylene glycol | 3.0 |
| Triethanolamine | 0.2 |
| Preservative, Pigment, Perfume | q.s. |
| Purified water | remainder |

Formulation Example 5 (Pack)

A pack was prepared using the compositions shown in Table 6 below according to a conventional method.

TABLE 6

| Component | Content (wt. %) |
|---|---|
| Compound of Formula 1 (Example) | 0.2 |
| Polyvinyl alcohol | 13.0 |
| Sodium carboxymethyl cellulose | 0.2 |
| Glycerine | 5.0 |
| Allantoin | 0.1 |
| Ethanol | 6.0 |
| PEG 12 nonylphenyl ether | 0.3 |
| Polysorbate 60 | 0.3 |
| Preservative, Pigment, Perfume | q.s. |
| Purified water | remainder |

The invention claimed is:

1. A hydroxyl pyranone compound represented by the following Formula 1:

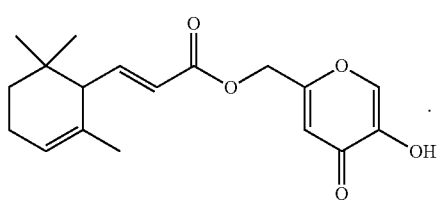

[Formula 1]

2. A method for preparing a hydroxyl pyranone compound of Formula 1 by reacting a pyranone compound of Formula 2 and a cyclohexenyl ester compound of Formula 3, which is represented by the following Reaction Scheme 1:

[Reaction Scheme 1]

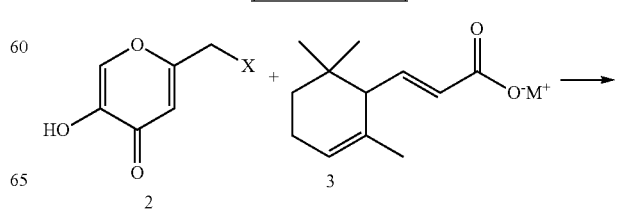

-continued
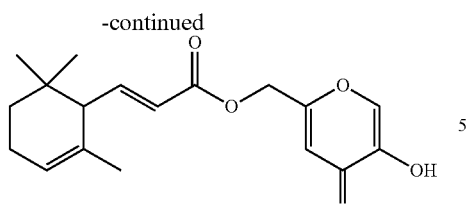
wherein X is a halogen element and M is Li, Na or K.
3. A cosmetic composition comprising a hydroxyl pyranone compound represented by the following Formula 1 as an active ingredient:
[Formula 1]
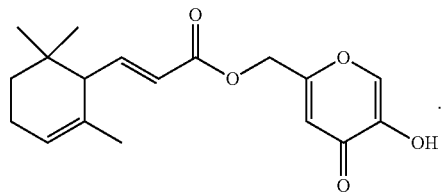
4. The cosmetic composition of claim 3, wherein the cosmetic composition has adipocyte differentiation promoting ability.
* * * * *